(12) United States Patent
Kronstedt et al.

(10) Patent No.: US 8,372,033 B2
(45) Date of Patent: Feb. 12, 2013

(54) CATHETER HAVING PROXIMAL HEAT SENSITIVE DEFLECTION MECHANISM AND RELATED METHODS OF USE AND MANUFACTURING

(75) Inventors: Brian Walter Kronstedt, Shoreview, MN (US); Martin Maitre Grasse, Minneapolis, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 984 days.

(21) Appl. No.: 12/347,133

(22) Filed: Dec. 31, 2008

(65) Prior Publication Data

US 2010/0168667 A1  Jul. 1, 2010

(51) Int. Cl.
*A61M 37/00* (2006.01)
(52) U.S. Cl. ............................................. 604/95.05
(58) Field of Classification Search ........... 604/95.05, 604/95.01, 528, 170.03; 29/428; 396/132; 600/151, 434, 146; 606/174
See application file for complete search history.

(56) References Cited

U.S. PATENT DOCUMENTS

| | | | |
|---|---|---|---|
| 5,125,895 A | 6/1992 | Buchbinder et al. | |
| 5,238,005 A | 8/1993 | Imran et al. | |
| 5,242,441 A | 9/1993 | Avitall | |
| 5,263,493 A | 11/1993 | Avitall | |
| 5,318,525 A | 6/1994 | West et al. | |
| 5,327,889 A | 7/1994 | Imran | |
| 5,327,905 A | 7/1994 | Avitall | |
| 5,354,297 A | 10/1994 | Avitall | |
| 5,389,072 A * | 2/1995 | Imran | 604/95.05 |
| 5,395,328 A | 3/1995 | Ockuly et al. | |
| 5,397,304 A | 3/1995 | Truckai | |
| 5,431,168 A | 7/1995 | Webster, Jr. | |
| 5,487,385 A | 1/1996 | Avitall | |
| 5,487,757 A | 1/1996 | Truckai et al. | |
| 5,545,200 A | 8/1996 | West et al. | |
| 5,562,619 A | 10/1996 | Mirarchi et al. | |
| 5,578,007 A | 11/1996 | Imran | |
| 5,611,777 A | 3/1997 | Bowden et al. | |
| 5,656,030 A | 8/1997 | Hunjan et al. | |
| 5,755,760 A | 5/1998 | Maguire et al. | |

(Continued)

OTHER PUBLICATIONS

Artificial Metal-Based Muscle, BioMetal Fiber, BMF Series, Toki Corporation, www.toki.co.jp/biometal, Sep. 2003.

(Continued)

*Primary Examiner* — Nicholas Lucchesi
*Assistant Examiner* — Brooke Matney
(74) *Attorney, Agent, or Firm* — Wiley Rein LLP

(57) ABSTRACT

Disclosed herein are various deflectable catheter systems that utilize materials having negative coefficients of thermal expansion to cause the catheter to deflect. A representative embodiment of the present invention includes a catheter having a heat-sensitive control member located outside the distal end of the catheter, but which is in mechanical communication with the distal end of the catheter such that heat may be applied to the control member to cause the distal portion to deflect. The applied heat, however, does not introduce any significant heat into the distal end of the catheter. The system may also include a processor to estimate an amount by which the catheter has been deflected based in part on temperature information of the control member, or even resistance measurements for the control member. The system may also include calibration systems and methods. Also disclosed herein are methods of use and methods of manufacturing system that utilize materials having negative coefficients of thermal expansion as control members.

25 Claims, 2 Drawing Sheets

U.S. PATENT DOCUMENTS

| | | | |
|---|---|---|---|
| 5,782,900 A | 7/1998 | de la Rama et al. |
| 5,807,249 A | 9/1998 | Qin et al. |
| 5,823,955 A | 10/1998 | Kuck et al. |
| 5,826,576 A | 10/1998 | West |
| 5,827,278 A | 10/1998 | Webster, Jr. |
| 5,836,947 A | 11/1998 | Fleischman et al. |
| 5,842,984 A | 12/1998 | Avitall |
| 5,843,076 A | 12/1998 | Webster, Jr. et al. |
| 5,843,152 A | 12/1998 | Tu et al. |
| 5,849,028 A | 12/1998 | Chen |
| 5,865,800 A | 2/1999 | Mirarchi et al. |
| 5,868,741 A | 2/1999 | Chia et al. |
| 5,876,399 A | 3/1999 | Chia et al. |
| 5,891,137 A | 4/1999 | Chia et al. |
| 5,893,884 A | 4/1999 | Tu |
| 5,895,417 A | 4/1999 | Pomeranz et al. |
| 5,897,529 A | 4/1999 | Ponzi |
| 5,897,554 A | 4/1999 | Chia et al. |
| 5,913,856 A | 6/1999 | Chia et al. |
| 5,916,213 A | 6/1999 | Haissaguerre et al. |
| 5,916,214 A | 6/1999 | Cosio et al. |
| 5,921,924 A | 7/1999 | Avitall |
| 5,931,811 A | 8/1999 | Haissaguerre et al. |
| 5,935,063 A | 8/1999 | Nguyen |
| 5,935,102 A | 8/1999 | Bowden et al. |
| 5,938,603 A | 8/1999 | Ponzi |
| 5,938,659 A | 8/1999 | Tu et al. |
| 5,938,694 A | 8/1999 | Jaraczewski et al. |
| 5,941,845 A | 8/1999 | Tu et al. |
| 5,944,690 A | 8/1999 | Falwell et al. |
| 5,951,471 A | 9/1999 | de la Rama et al. |
| 5,971,968 A | 10/1999 | Tu et al. |
| 5,987,344 A | 11/1999 | West |
| 5,993,462 A | 11/1999 | Pomeranz et al. |
| 6,001,095 A | 12/1999 | de la Rama et al. |
| 6,002,955 A | 12/1999 | Willems et al. |
| 6,006,123 A | 12/1999 | Nguyen et al. |
| 6,048,329 A | 4/2000 | Thompson et al. |
| 6,059,739 A | 5/2000 | Baumann |
| 6,064,902 A | 5/2000 | Haissaguerre et al. |
| 6,066,125 A | 5/2000 | Webster, Jr. |
| 6,068,629 A | 5/2000 | Haissaguerre et al. |
| 6,071,279 A | 6/2000 | Whayne et al. |
| 6,083,170 A | 7/2000 | Ben-Haim |
| 6,083,222 A | 7/2000 | Klein et al. |
| 6,117,101 A | 9/2000 | Diederich et al. |
| 6,123,699 A | 9/2000 | Webster, Jr. |
| 6,138,043 A | 10/2000 | Avitall |
| 6,146,338 A | 11/2000 | Gardeski et al. |
| 6,156,034 A | 12/2000 | Cosio et al. |
| 6,169,916 B1 | 1/2001 | West |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,200,315 B1 | 3/2001 | Gaiser et al. |
| 6,203,507 B1 | 3/2001 | Wadsworth et al. |
| 6,203,525 B1 | 3/2001 | Whayne et al. |
| 6,210,407 B1 | 4/2001 | Webster |
| 6,217,528 B1 | 4/2001 | Koblish et al. |
| 6,221,070 B1 | 4/2001 | Tu et al. |
| 6,241,727 B1 | 6/2001 | Tu et al. |
| 6,308,091 B1 | 10/2001 | Avitall |
| 6,314,963 B1 | 11/2001 | Vaska et al. |
| 6,325,797 B1 | 12/2001 | Stewart et al. |
| 6,383,151 B1 | 5/2002 | Diederich et al. |
| 6,434,333 B2 * | 8/2002 | Tanaka et al. ............ 396/132 |
| 6,500,167 B1 | 12/2002 | Webster, Jr. |
| 6,702,811 B2 | 3/2004 | Stewart et al. |
| 6,743,227 B2 | 6/2004 | Seraj et al. |
| 6,783,521 B2 | 8/2004 | Ponzi et al. |
| 6,802,840 B2 | 10/2004 | Chin et al. |
| 6,837,886 B2 | 1/2005 | Collins et al. |
| 6,997,870 B2 | 2/2006 | Couvillon, Jr. |
| 2002/0087169 A1 | 7/2002 | Brock et al. |
| 2006/0084945 A1 | 4/2006 | Moll et al. |

OTHER PUBLICATIONS

Dynalloy, Inc., Technical Characteristics of Flexinol, Actuator Wires, Nickel-Titanium Alloy Physical Properties, pp. 1-12 (1997).

* cited by examiner

CATHETER HAVING PROXIMAL HEAT SENSITIVE DEFLECTION MECHANISM AND RELATED METHODS OF USE AND MANUFACTURING

BACKGROUND OF THE INVENTION a. Field of the Invention

The instant invention relates to deflectable catheters, including introducer catheters and treatment catheters, as well as methods of use and methods of manufacturing relating thereto.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

To increase the ability to move and navigate a catheter within a patient's body, steerable catheters have been designed. Steerable catheters are often manipulated by selectively tensioning one or more pull wires running along the length of the catheter, typically offset from a central axis of the catheter, thereby deflecting the distal end of the steerable catheter in one or more planes. These pull wires are often attached to a metallic catheter component located at the distal end of the catheter, such as one of the electrodes carried on the distal end of the catheter or a pull ring incorporated in the catheter. Placing a pull wire in tension causes the distal end of the catheter to deflect in at least one plane. In this fashion, the catheter can be navigated through the tortuous path of a patient's vasculature to a target site. Because of the length of the path that a catheter may need to travel to reach a target site, however, greater control over deflectability is desired.

BRIEF SUMMARY OF THE INVENTION

Disclosed herein in one embodiment for a deflectable catheter having a catheter body with a proximal end, a catheter shaft, and a distal portion. A control unit is coupled to the proximal end of the catheter body, and an elongate tensioning element extends from the control unit through the proximal end, through the catheter shaft and to the distal portion of the catheter body. The elongate tensioning element is secured at a point in the distal portion such that when pulled, the distal portion deflects. A heat-sensitive control member is located in the control unit and is coupled to a proximal end of the elongate tensioning element. A heat source (including without limitation, heat that results from application of electrical current) is positioned to apply heat to the heat-sensitive member, which has a negative coefficient of thermal expansion such that when heat is applied to the heat-sensitive member, the heat-sensitive control member contracts, placing the elongate tensioning element in tension, and thereby deflecting the distal portion of the catheter. Optionally, the heat source comprises a first conductor electrically coupled to a proximal end of the heat-sensitive member, a second conductor electrically coupled to a distal end of the heat-sensitive member; and a power supply electrically coupled to the first and second conductors to deliver an amount of current to the heat-sensitive control member to heat the heat-sensitive control member. Additionally and optionally, a cooling source may be disposed within the control unit such that when activated, the cooling source cools the control member and helps dissipate any heat in the control member, causing the control member to expand and, in turn, exerting a force on the elongate tensioning element to cause the catheter to deflect. The heat-sensitive control member may be made of a nickel titanium alloy or any other metal or alloy that has a negative coefficient of thermal expansion. Alternatively the heat-sensitive control member may be made of a nickel titanium alloy formed in a helix shape. The control unit may optionally use one or more pulleys around which the heat-sensitive control member may be wrapped, in whole or in part. While the control unit may be a catheter handle, it may also be sized and shaped to fit on a moveable chassis. Optionally, the deflectable catheter may include a temperature sensor to measure the temperature of the heat-sensitive member. Further, the deflectable catheter may include a processor to estimate an amount by which the catheter has been deflected based in part on an output of the temperature sensor. A coupler may be used to couple a distal end of the heat-sensitive control member with the proximal end of the elongate tensioning element; preferably, the coupler provides thermal and electrical isolation between the heat-sensitive control member and the elongate tensioning element.

In another embodiment of the present invention, a method of deflecting a catheter is disclosed. A catheter is provided, which catheter has: a catheter body with a proximal end, a catheter shaft, and a distal portion. A catheter control handle is coupled to the proximal end of the catheter body, and an elongate tensioning element extends from the control handle through the proximal end, through the catheter shaft and to the distal portion of the catheter body. The elongate tensioning element is secured at a point in the distal portion such that when pulled, the distal portion deflects. The elongate flexible member has a negative coefficient of thermal expansion and is disposed in the control handle, and it is coupled to a proximal end of the elongate tensioning element. The elongate flexible member in the catheter control handle is heated to cause the elongate flexible member to contract and thereby pull the elongate tensioning element to deflect the catheter. While the elongate flexible member may be heated using any known heat technique, one way to heat it is to apply a current to the elongate flexible member using a power supply that is coupled to opposite ends of the elongate flexible member. The elongate flexible member may be cooled using known cooling techniques also to deflect the catheter. Desirably, the elongate flexible member is sized and configured to deflect the catheter at least 180 degrees. The elongate flexible member may be made of any material having a negative coefficient of thermal expansion, and may be made of a nickel titanium alloy. The catheter handle may include at least one control knob, such that the user may adjust the control knob to apply heat to the elongate flexible member in the catheter control handle to deflect the catheter.

The present invention may optionally include one or more calibration related procedures. For example, the elongate flexible member may be heated to a plurality of increasing temperatures, and the amount of deflection of the distal portion of the catheter may be measured for each of the plurality of increasing temperatures. Each measured amount of deflection can then be associated with the corresponding temperature at which the deflection was measured. The associated temperature and deflection measurements may be stored in a storage medium, for example, in table or graphical form. When the elongate flexible member is heated to a particular temperature, which temperature may be confirmed by measurement, the measured temperature and the stored associated temperature and deflection measurements may be used to estimate the amount by which the catheter has been deflected. This estimation may be made using a computer processor. Optionally, it may be desired to have additional data to reflect differences associated with increasing and decreasing temperature trends. For example, in addition and/or alternatively to the increasing temperatures previously described, the elongate flexible member may be allowed to cool to a plurality of decreasing temperatures, and the amount of deflection of the distal portion of the catheter may be measured at each of the plurality of decreasing temperatures. Optionally, a cooling mechanism to dissipate heat in the elongate flexible member may also be used to aid in the cooling process, for example, to control the rate of cooling. Each measured amount of deflection may be associated with the temperature at which the deflection was measured, along with information to reflect that the deflection was measured while the temperature was decreasing. This associated measurement information for the decreasing temperatures may then be stored in a storage medium, for example, in graphical or tabular form. It may be used to supplement the associated measurement information for the increasing temperatures.

Alternatively, a calibration procedure of the present invention may utilize resistance measurements since resistance typically varies with length. For example, the elongate flexible member may be heated or cooled to a plurality of temperatures and the resistance of the elongate flexible member may be measured at each of the plurality of temperatures. A correlation between resistance and length may be used to estimate an amount by which the catheter has been deflected. Alternatively, the elongate flexible member may be heated or cooled to deflect the catheter to each of a plurality of deflected positions, and the resistance of the elongate flexible member may be measured. The amount of deflection of the catheter at each of the plurality of deflected positions may be measured, and each measured amount of resistance may be associated with the corresponding measured amount of deflection. This associated resistance and deflection measurements may be stored in a storage medium, for example in graphical or tabular form. Then the elongate flexible member may be heated or cooled, and a resistance measurement may be made to estimate the amount of deflection; more particularly, the measured resistance and the stored associated resistance and deflection measurements are used to estimate an amount by which the catheter has been deflected. The estimation may be made using a computer processor and associated software.

In yet another embodiment of the present invention, a method of manufacturing a deflectable catheter is disclosed. A catheter is formed having a catheter body with a proximal end, a catheter shaft, a distal portion, and an elongate tensioning element that extends from the proximal end through the catheter shaft and to the distal portion of the catheter body, said elongate tensioning element being secured to the catheter such that a force imposed on the elongate tensioning element causes the catheter to defect. A catheter control unit is formed, and a control member is positioned inside the control unit such that one end of the control member is fixed relative to the control unit and the other end is free to move with respect to the control unit. The control member is made using material having a negative coefficient of thermal expansion such that when heat is applied, the control member contracts. A heat source is provided within the control unit such that when activated, the heat source heats the control member and causes it to contract. The catheter is secured to the control unit and the elongate tensioning element of the catheter is disposed in mechanical communication with the control member such that when the control member is heated, a force is imposed on the elongate tensioning element to cause the catheter to deflect. Optionally, the heat source may be installed as follows. The a first conductor may be installed into the control unit that is electrically coupled to a proximal end of the control member, and a second conductor is installed into the control unit that is electrically coupled to a distal end of the control member. A connection may optionally be provided to electrically couple to the first and second conductors which can be connected to a power supply for delivering sufficient current to the control member to heat the control member. Additionally and optionally, a cooling source may be provided within the control unit such that when activated, the cooling source cools the control member and helps dissipate any heat in the control member, causing the control member to expand and, in turn, exerting a force on the elongate tensioning element to cause the catheter to deflect.

A technical advantage of the present invention is that by taking advantage of the control element's unique thermal properties, greater control over the catheter can be achieved. For example, by maintaining a steady temperature of the control member, the control member remains in a fixed position, which correspondingly maintains the elongate tension element in a fixed position. In this sense, the control member can be used to "lock" the position of the catheter.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
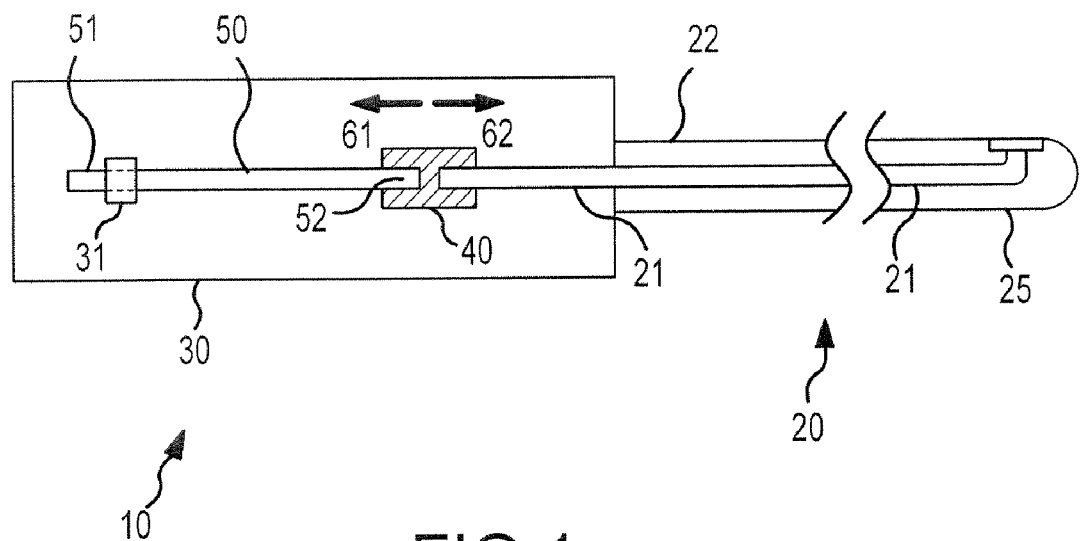
FIG. 1 is a schematic representation of a catheter system in accordance with an embodiment of the present invention.

The present invention permits a catheter to be deflected using a heat source by placing a control member in a control unit wherein heat may be applied to and removed from the control member. The present invention takes advantage of materials having negative coefficients of thermal expansion and then uses heat and/or cooling to control catheter manipulation. The present invention can also utilize a cooling source to deflect the catheter.

Aspects of the present invention involve a steerable and/or shapable catheter that employs a heat-sensitive control mechanism to change the shape of some portion of the catheter to perform a procedure and/or steer the catheter as it is being directed toward some location in the body. In one particular arrangement, the catheter includes a control mechanism including a control member made of a material having a negative coefficient of thermal expansion such that, through heating (e.g., application of heat) and cooling (e.g., removal of heat, cooling, etc.) the control mechanism can deflect a catheter. The control member is located at the proximal end of the catheter, typically in a control unit which is always located outside the patient's body. Thus, by managing the temperature of the control member, the catheter shape may be manipulated into a particular shape and thereby maneuvered into a desired location or arranged into a desired shape for a procedure at the target tissue site.

In connection with FIG. 1, a catheter system according to some embodiments of the present invention will now be described. The catheter system 10 generally includes a control unit 30 and a catheter 20 having a proximal portion 22 and a distal portion 25. The control unit 30 includes a control member 50 that is disposed within control unit 30 such that the proximal end 51 of the control member 50 is secured to the control unit by a securing device 31. Securing device 31 may be a screw, a weld, an epoxy deposit, a clamp, a tensioning device or another connector suitable to secure the control member 50 to the control unit 30.

The distal end 52 of the control member 50 is not fixed, such that the distal end 52 is free to move relative to the proximal end 51 (e.g., via expansion and contraction of control member 50). The distal end 52 is coupled to an elongate tensioning element 21 (for example, stainless steel wire) that extends from the control unit 30 through the proximal portion 22 of the catheter 20 to the distal portion 25 of the catheter 20. As one of ordinary skill in the art will appreciate, the elongate tensioning element 21 may be secured at any point along catheter 20 (e.g., to a pull ring embedded in the wall of catheter 20), but for illustration purposes, it is shown as being secured to the distal portion 25 of catheter 20.

The control member 50 is coupled to the elongate tensioning element 21 using a coupler 40. In some embodiments of the invention, coupler 40 is made of a thermally and electrically non-conductive material so as to thermally isolate the control member 50 from the elongate tension member 21; for example, the coupler 40 may be made of a rigid polymer or plastic having an H- or I-shape, and the distal end 52 of the control member 50 and the proximal end of the elongate tensioning member 21 may be each secured to the coupler 40 using an epoxy or other material known in the art. Of course, coupler 40 may have other shapes and may be made of other materials, including for example a tubular shaped coupler that is temporarily or permanently secured to each of the members being joined, for example via crimping.

A heat source (not shown) may be used to apply heat to control member 50, and optionally, a cooling source (not shown) may be used to remove heat from control member 50. When heat is applied to the control member 50, the negative coefficient of thermal expansion causes control member 50 to contract in direction 61. This, in turn, pulls elongate tensioning member 21, placing elongate tensioning member 21 in tension and thereby deflecting distal portion 25 of the catheter 20. Similarly, when the heat source is deactivated and/or the cool source is activated, and the temperature of control member 50 is allowed to return to an unheated state or cooled to a cooled temperature, the elongate control member 50 expands in a direction 62, thereby releasing the tension on elongate tensioning member 21 and permitting the distal portion 25 of catheter 20 to return to an undeflected state. The degree to which elongate control member 50 may expand after the heat source is removed may vary depending on the same and composition. It is contemplated that a stretching force may be applied to help the elongate control member 50 return to its initial expanded state. For example, a stretching member (not shown) may be used to apply a stretching force to the elongate member 50 in the direction of 62; the stretching member could be in the form of a pull wire, and alternatively, could be an elongate member that has a negative coefficient of thermal expansion that could receive heat from a heat source to cause the stretching member to contract and simultaneously apply a stretching force. Alternatively, a second control member may be used to deflect the distal portion 25 of catheter 20 into the opposite direction which may exert a stretching force on the first control member.

While the heat source is not shown in connection with FIG. 1, one of ordinary skill will appreciate that a variety of heat sources may be used, including, without limitation, a power supply having two electrodes, one of which is electrically coupled to distal end 51 of elongate member 50 and the other of which is electrically coupled to proximal end 52. Alternatively, or in addition, a separate heating element that is located sufficiently close to elongate member 50 to transfer heat thereto may be positioned within the control unit. Of course, other heat sources are regarded as within the spirit and scope of the present invention as well. Similarly, a variety of cooling sources can be used in the present invention, including for example, a cooling fluid and/or thermally-coupled cooling supply.

For illustration purposes, a single control member 50 and a single elongate tensioning member 21 are depicted in catheter system 10 of FIG. 1. It is contemplated, however, that the present invention may be used with a plurality of control members coupled to a plurality of tensioning members within a single catheter. For example, each control member could be paired with another control member and arranged so as to act in opposition to one another; in other words, one control member can be used to deflect the catheter in a first direction, and its paired control member can be used to deflect the catheter back in the opposite direction. Though not illustrated, it is also contemplated that a plurality of control members may be coupled in series or in parallel to a single tensioning member. For example, two or more heat-sensitive control members may be aligned with each other, either by direct coupling to each other, or indirect coupling using intervening linkages, where the linkages are not characterized by a negative coefficient of thermal expansion.

Optionally, a temperature sensor (not shown) may be used to measure the temperature of control member 50. The measured temperature may be used to estimate the degree of contraction of the control member 50, which allows an estimation of the degree of deflection of the distal end 25 of the catheter 20. In one embodiment, the temperature sensor may comprise a thermistor or thermocouple that is thermally coupled to control member 50. Of course, other temperature sensors may be used as well. Optionally, a processor (not shown) uses the measured temperature of the control member 50 to estimate the distance by which the distal end 52 of the control member 50 has moved and/or to estimate the deflection of the catheter that may result from the contraction undergone by the control member 50. The processor may comprise a conventional general purpose computer, a special purpose computer, a distributed computer, or any other type of computer; the processor may comprise one or more processors, such as a single central-processing unit, or a plurality of processing units, commonly referred to as a parallel processing environment.

Optionally, the system may include a device to measure the impedance of the control member 50 as measured by two electrodes at opposite ends of the control member 50. Since impedance can be estimated in part based on a cross-sectional surface area and distance, a processor can use the measured impedance to estimate the distance by which the distal end 52 of the control member 50 has moved and/or to estimate the deflection of the catheter that may result from the contraction undergone by the control member 50. To assist in estimating the cross sectional area, the system may optionally include a device to measure the outer dimensions of the control member 50, which measurement may then be used by the processor in calculating distances and/or deflections.

For illustration purposes, the control member 50 is depicted as a wire, but it is contemplated that other shapes and sizes may be used, including for example, elongate, non-wire shapes, such as a helix.

While the catheter 20 in the embodiment of FIG. 1 may be depicted as a treatment catheter, the catheter may also take the form of an introducer catheter, an electrophysiological catheter, a diagnostic catheter, a mapping catheter and the like.

Control unit 10 may take the form of a catheter handle or it may be a control unit larger or smaller in size than a catheter handle that would fit into a typically-sized hand of an operator. In addition, control unit 10 may be unmounted, or it may be mounted permanently or removably mounted to a robotic housing that may be directly or indirectly slidable or otherwise moveable.

Figure 2:
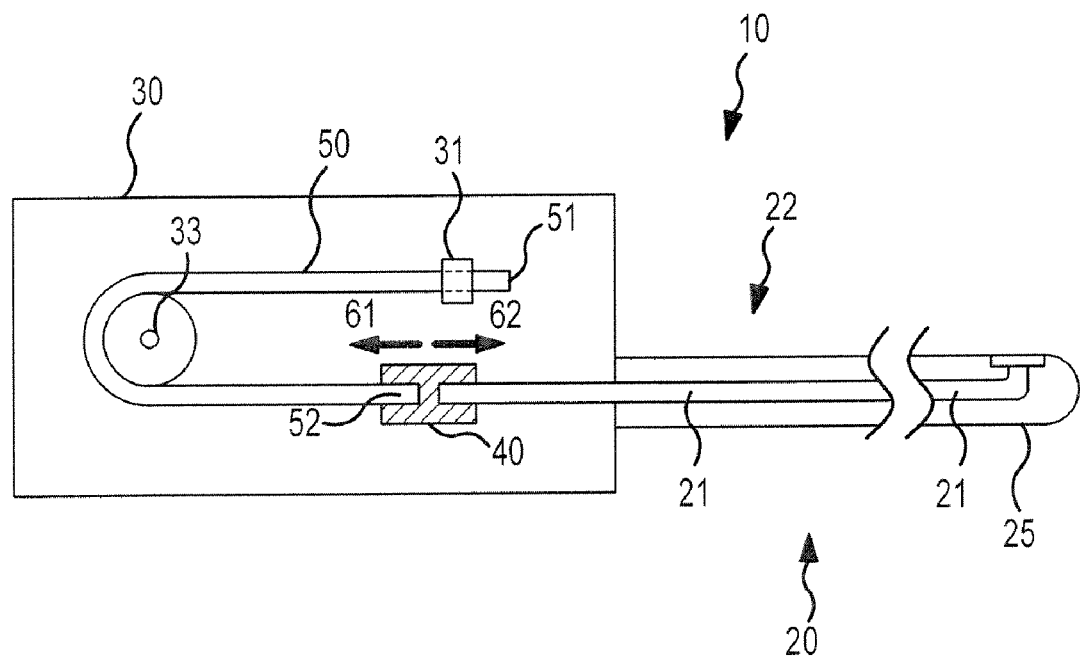
FIG. 2 is a schematic representation of a catheter system in accordance with another embodiment of the present invention.

In connection with FIG. 2, a catheter system according to other embodiments of the present invention will now be described. The catheter system depicted in FIG. 2 is similar to the catheter system depicted in FIG. 1. Control unit 30 includes a pulley 33 about which control member 50 may be wrapped such that control member may freely move with the assistance of pulley 33. The distal end 52 of the elongate control member 50 is not fixed, such that the distal end 52 is free to move relative to the proximal end 51 (e.g., via expansion and contraction of elongate control member 50). The distal end 52 is coupled to an elongate tensioning element 21 (for example, stainless steel wire) that extends from the control unit 30 through the proximal portion 22 of the catheter 20 to the distal portion 25 of the catheter 20. As one of ordinary skill in the art will appreciate, the elongate tensioning element 21 may be secured at any point along catheter 20, but for illustration purposes, it is shown as being secured to the distal portion 25 of catheter 20.

The elongate control member 50 is coupled to the elongate tensioning element 21 using a coupler 40. In some embodiments of the invention, coupler 40 is made of a thermally and electrically non-conductive material; for example, coupler 40 may be made of a rigid polymer or plastic having an H- or I-shape and the distal end 52 of the elongate control member 50 and the proximal end of the elongate tensioning member 21 may be secured to the coupler 40 using an epoxy or other material known in the art. Of course, coupler 40 may have other shapes and may be made of other materials, including for example a plastic, tubular shaped coupler that is temporarily or permanently secured to each of the members being joined, for example via crimping.

A heat source (not shown) may be used to apply heat to elongate control member 50, and optionally, a cooling source (not shown) may be used to remove heat from control member 50. When heat is applied to the elongate control member 50, the negative coefficient of thermal expansion causes elongate control member 50 to contract about the pulley 33, resulting in a movement of the distal end 52 in the direction 61. This, in turn, pulls the elongate tensioning member 21, thereby placing elongate tensioning member 21 in tension and deflecting the distal portion 25 of the catheter 20. Similarly, when the heat source is deactivated and/or the cool source is activated, and the temperature of elongate control member 50 is allowed to return to an unheated state or cooled to a lower temperature, the elongate control member 50 expands in a direction 62 thereby releasing the tension, and/or exerting forces, on elongate tensioning member 21 and deflecting the distal portion 25 of catheter 20 in the opposite direction when compared to the heated deflection. The degree to which elongate control member 50 may expand after the heat source is removed may vary depending on the same and composition. It is contemplated that a stretching force may be applied to help the elongate control member 50 return to its initial expanded state. For example, a stretching member (not shown) may be used to apply a stretching force to the elongate member 50 in the direction of 62; the stretching member could be in the form of a pull wire, and alternatively, could be an elongate member that has a negative coefficient of thermal expansion that could receive heat from a heat source to cause the stretching member to contract and simultaneously apply a stretching force.

While the heat source is not shown in connection with FIG. 2, one of ordinary skill will appreciate that a variety of heat sources may be used, including, without limitation, a power supply having two electrodes, one of which is electrically coupled to distal end 51 of elongate member 50 and the other of which is electrically coupled to proximal end 52. Alternatively, or in addition, a separate heating element that is located sufficiently close to elongate member 50 to transfer heat thereto may be positioned within the control unit. Of course, other heat sources are regarded as within the spirit and scope of the present invention as well. Similarly, a variety of cooling sources can be used in the present invention, including for example, a cooling fluid and/or thermally-coupled cooling supply.

For illustration purposes, a single control member 50 and a single elongate tensioning member 21 are depicted in catheter system 10 of FIG. 2. It is contemplated, however, that the present invention may be used with a plurality of control members coupled to a plurality of tensioning members within a single catheter. For example, each control member could be paired with another control member and arranged so as to act in opposition to one another; in other words, one control member can be used to deflect the catheter in a first direction, and its paired control member can be used to deflect the catheter back in the opposite direction. Though not illustrated, it is also contemplated that a plurality of control members may be coupled in series or in parallel to a single tensioning member. For example two or more heat-sensitive control members may be aligned with each other, either by direct coupling to each other, or indirect coupling using intervening linkages, where the linkages are not characterized by a negative coefficient of thermal expansion.

Similarly, for illustration purposes, only a single pulley 33 is depicted in the catheter system of FIG. 2. It is contemplated, however, that a plurality of pulleys may be used. In addition, the pulley preferably is a wheel that rotates and that has a groove and two flanges to hold the control member in the groove; one of ordinary skill however, will appreciate that a fixed wheel-like device, preferably with a groove, may be used consistent with the teachings of this invention. In addition, it is contemplated that control member 50 may be wrapped in whole or in part about the pulley 33. For example, control member 50 may be wrapped about 25%, about 50% or more about the pulley 33. When a pulley is being used, it is preferred that the control member 50 be a wire member as illustrated in FIG. 2.

Optionally, a temperature sensor (not shown) may be used to measure the temperature of control member 50. The measured temperature may be used to estimate the degree of contraction of the control member 50, which allows an estimation of the degree of deflection of the distal end 25 of the catheter 20. In one embodiment, the temperature sensor may comprise a thermistor or thermocouple that is thermally coupled to control member 50. Of course, other temperature sensors may be used as well. Optionally, a processor uses the measured temperature of the control member 50 to estimate the distance by which the distal end 52 of the control member 50 has moved and/or to estimate the deflection of the catheter that may result from the contraction undergone by the control member 50.

Optionally, the system may include a device to measure the impedance of the control member 50 as measured by two electrodes at opposite ends of the control member 50. Since impedance can be estimated in part based on a cross-sectional surface area and distance, a processor can used the measured impedance to estimate the distance by which the distal end 52 of the control member 50 has moved, and/or to estimate the deflection of the catheter that may result from the contraction undergone by the control member 50. To assist in estimating the cross sectional area, the system may optionally include a device to measure the outer dimensions of the control member 50, which measurement may then be used by the processor in calculating distances and/or deflections.

For illustration purposes, the control member 50 is depicted as a string, but it is contemplated that other shapes and sizes may be used, including for example, elongate, non-wire shapes, such as a helix.

While the catheter 20 in the embodiment of FIG. 2 may be depicted as a treatment catheter, the catheter may also take the form of an introducer catheter, an electrophysiological catheter, a diagnostic catheter, a mapping catheter and the like.

Control unit 10 may take the form of a catheter handle or it may be a control unit larger or smaller in size than a catheter handle that would fit into a typically-sized hand of an operator. In addition, control unit 10 may be unmounted, or it may be mounted permanently or removably mounted to a robotic housing that may be directly or indirectly slidable or otherwise moveable.

Figure 3:
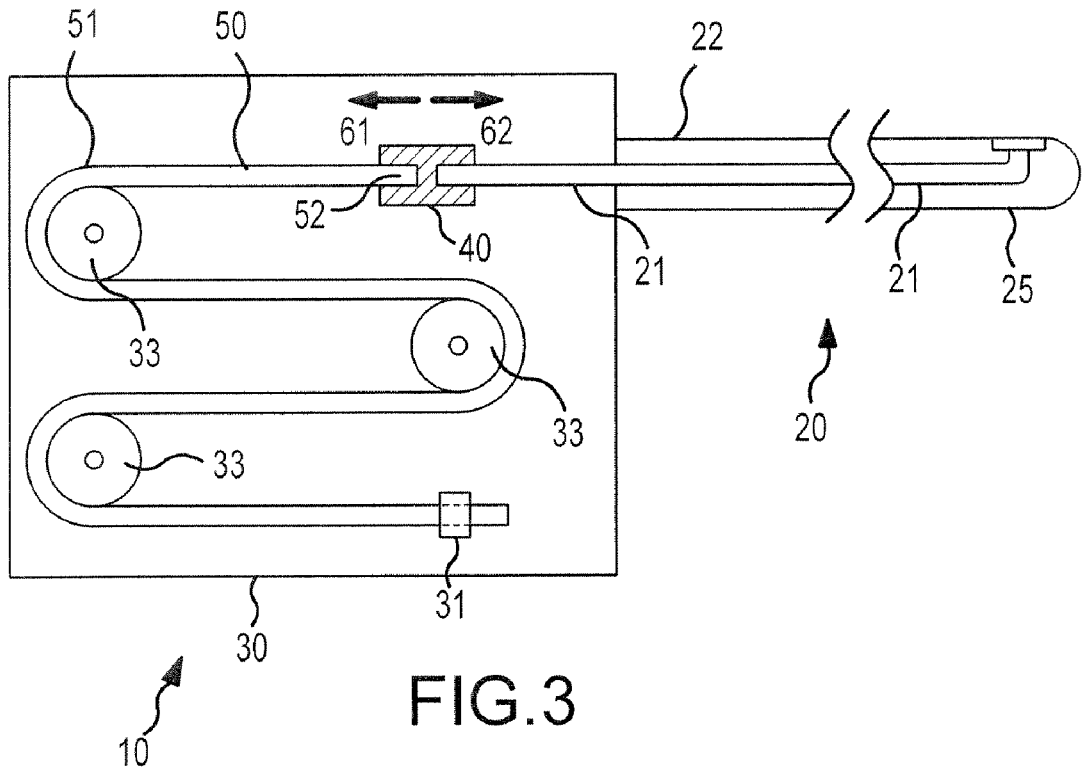
FIG. 3 is a schematic representation of a catheter system in accordance with yet another embodiment of the present invention.

In FIG. 3, another embodiment of the catheter system of the present invention is illustrated. The system of FIG. 3 is similar to the embodiment depicted in FIG. 2, except that three pulleys 33 are used, which will permit a longer control member 50 to be used. This, in turn, allows greater contraction of control member 50, which facilitates greater deflection of the distal end 25 of the catheter 20. Each of the three pulleys 33 may have the same or different diameters. The structural description and the operation are otherwise identical as that discussed above in connection with the embodiment depicted in FIG. 2.

Figure 4:
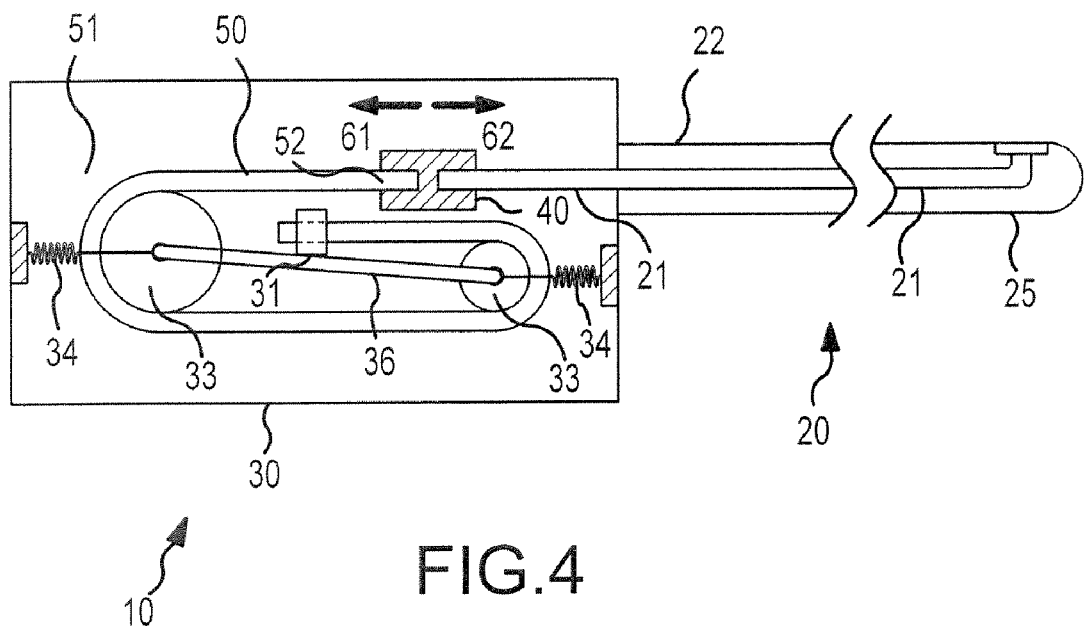
FIG. 4 is a schematic representation of a catheter system in accordance with yet another embodiment of the present invention.

In FIG. 4, yet another embodiment of the catheter system of the present invention is illustrated. The system of FIG. 4 is nearly identical to the embodiment depicted in FIG. 2, except that two pulleys 33 are used, each of which is suspended under spring tension by springs 34, which are mounted to control unit 30. Each of the two pulleys 33 may have the same or different diameters, and further, one or both of the pulleys may be mounted on a track 36 to permit the pulleys to move laterally with respect to the springs and each other. The springs 34 would preferably have a spring constant that can generate an opposing force that is about the same or greater than the force generated by the contraction of control member 50. The structural description and the operation are otherwise substantially identical as that discussed above in connection with the embodiment depicted in FIG. 2.

In each of the embodiments described above, the catheter systems may be modified to permit manual catheter adjustments. For example, the control units above may include a coupler 40 that permits the control element 50 and/or the elongate tension element 21 to be disconnected so that a manual control may be used to manipulate the elongate tension elements either directly (by coupling to the elongate tension elements) or indirectly by coupling to the coupler 40. Alternatively, the systems above may be modified so that the distal end 51 of the control element 50 may be physically moved (e.g., without temperature changes) to manipulate the elongate tension element 21, thereby providing manual control over the catheter.

The present invention also includes a method of use in which will now be described in connection with the embodiment illustrated in FIG. 1, in which the catheter system 10 is used to perform diagnostic procedures. The distal portion 25 of the catheter 20 is introduced into the body of a patient, for example by using an introducer catheter (not shown). Control unit 30 remains outside the body. A heat source (not shown) is activated to apply heat to control member 50 to raise its temperature to a point at which the control member 50 contracts, thereby causing the distal portion 25 of catheter 20 to deflect. The heat source applied may be any of a number of heat sources, including, without limitation heated air, heated liquid, a separate heating element or a power supply that delivers power to the control member 50 using two electrodes on opposite ends of the control member. When current is used, and depending on the composition for control element 50, it is possible to achieve a desired level of deflection in as short as one second. Optionally, a cooling source (not shown) is activated to remove heat from control member 50 to decrease its temperature to a point at which the control member 50 expands, thereby causing the distal portion 25 of catheter 20 to deflect. The cooling source may be any number of cooling sources, including, for example, a cooling fluid in combination with a heat exchanger.

Optionally, the system may use a temperature sensor (not shown) to measure the temperature of control member 50 and a processor may use the measured temperature to estimate the distance by which the distal end 52 of the control member 50 has moved and/or the amount of deflection that the catheter has undergone. The temperature sensor may also be used to monitor the temperature of the control member 50, and by maintaining a constant temperature, the catheter's relative position of deflection can be maintained.

Optionally, the system may use a device to measure the impedance of the control member 50 as measured between opposite ends of the control member 50. A processor may use the measured impedance to estimate the distance by which the distal end 52 of the control member 50 has moved and/or the amount of deflection by which the catheter has undergone. The system may also and optionally include a device to measure the outer measurements of the control member 50 as it expands and contracts.

In an embodiment in which the control unit is a catheter handle, the control unit may also include controls such as rotary knobs, slide knobs and/or a push adjustment knob. Preferably, the controls are marked to correspond to the general degree of catheter deflection, but the controls could also be marked by temperature, which the system could then correlate to the catheter deflection. In some aspects, a control knob exists for each control member housed in the catheter handle.

In adjusting the temperature of the control member, it is contemplated that the user may prefer to develop a calibration table and/or chart that is used for future operations of the catheter. For example, the temperature of the control member may be slowly increased and the absolute position of the catheter can be measured to correlate temperature with catheter deflection. Of course, it is not unusual for the amount of deflection to depend on whether the temperature is being increased or decreased. This is because many materials with a negative coefficient of thermal expansion experience a hysteresis in the temperature-displacement curve. By progressively increasing the temperature through a plurality of temperature points and measuring the relative amounts of deflection for each of the temperatures, and then progressively decreasing the temperature at a plurality of temperature points and measuring the relative amounts of deflection, one can develop a reliable chart and/or table for use in estimating catheter deflection for a given temperature and modality (e.g., achieved via heating or achieved via cooling). These calibration measurements may be taken with a separate temperature sensor that provides a real time estimate for the temperature of the control member, but it is also possible to generate a calibration curve using the relative position of the control knobs The control member described above is preferably made of a material that exhibits a negative coefficient of thermal expansion when exposed to heat. A material suitable for this purpose is a variety of nickel titanium alloys. One such alloy is manufactured and sold under the trademark Flexinol™ by Dynalloy, Inc., of California. It is believed that heating Flexinol changes its crystalline structure causing it to shorten itself—that is, Flexinol has a negative coefficient of thermal expansion. Flexinol wire is available in diameters ranging from about 0.001 to about 0.020 inches, and begins to contract at a temperature of about 70° C. Flexinol is typically flexible in an unheated state, but can become rigid after being heated to the point of contraction. The contraction time can be as fast as about 1 second, and the extent of contraction may be as much as about 4% to about 5%. The heat can be provided by any number of heat sources, including heating elements, air, liquid, etc. One way to heat Flexinol is to use a power supply to pass current therethrough. Current may be applied in the range from about 20 mA (for wire about 0.001 inches in diameter) to about 4 A (for wire about 0.20 inches in diameter). While Flexinol wire may be used, Flexinol may be used to form a control member having other shapes, including non-wire based elongate shapes.

Another material having a negative coefficient of thermal expansion that may be used with the present invention is the BMF™ series biometal fiber by Toki Corporation of Japan, which is also made of a nickel titanium alloy. The biometal fiber ranges from about 0.05 mm to about 0.15 mm in diameter, and begins to contract when the temperature reaches about 70° C. Current may be applied in the range from 80 mA to about 340 mA, and at voltages from about 20V to about 40V. The percentage of contraction/elongation is about 5% or more of the overall length.

Another material having a negative coefficient of thermal expansion is the BMX series biometal helix by Toki Corporation of Japan, which is also made of a nickel titanium alloy. The biometal helix ranges in size from about 0.2 mm to about 0.62 mm in diameter for the helix, with a wire size ranging from about 0.2 mm to about 0.62 mm, and begins to contract when the temperature reaches about 50° C. to about 60° C. Current may be applied in the range from about 50 mA to about 300 mA, and at voltages from about 20V to about 40V. The percentage of contraction can be as much as about 30% to about 70% of the overall length.

Other materials may also be used, including without limitation other nickel-titanium alloys. For example, mixtures of about 30% to about 70% nickel and about 70% to about 30% titanium, and more preferably about 40% to about 60% nickel and about 60% to about 40% titanium, and most preferably about 50-50 nickel and titanium are suitable for use in control members according to the present invention.

Control unit 10 can be used to heat the control member 50, which in turn contracts, pulls on the elongate tensioning element 21 and deflects the distal portion 25 of the catheter 20. Current may be applied using direct current (DC), alternating current (AC) and/or pulse techniques. Pulsing current may help better control the heat, and may be achieved using a variety of known techniques, including for example, delivering current in pulses in which the duty cycle is variable (i.e., pulse width modulation). Pulsing current supplies with variable duty cycles are widely available and may be constructed using a the 555 general purpose timing IC, such as the NE555, SE555, and/or SA555 circuits available through SGS Thompson Microelectronics, among many other suppliers.

In a preferred embodiment, the control member is a segment of wire, which may be used in a straight configuration or which may be in contact with one, two or more pulleys. The use of pulleys will permit a longer segment of wire to fit within a space that is a fraction of the length of the longer segment. For example, the use of one pulley will permit the wire to change direction, which can effectively permit a wire having a distance of D to be placed in a control unit or handle that has a length of about ½ of D. In a different embodiment, the control member may comprise a helix, similar to a spring in appearance.

A variety of heat sources can be used in the present invention, including for example, heated air, heated liquid, a thermally-coupled heat supply and/or a power supply. In one embodiment, an electrical power supply may be electrically coupled using two electrodes, one placed at each end of the temperature-sensitive, control member. The power supply may utilize alternating current, direct current or pulse current. Similarly, a variety of cooling sources can be used in the present invention, including for example, a cooling fluid and/or thermally-coupled cooling supply.

With the present invention, it is desirable for the temperature sensitive control member to be placed outside the distal portion of the catheter. Placing the control member inside the distal portion of the catheter is undesirable for many reasons. First, there are space limitations in the distal portion of a typical catheter that will limit the amount of control that the member would have over the deflectable catheter. For example, in a case of a catheter having multiple pull wires, it is not unusual for the pull wires to be displaced as much as 2 inches in order to fully deflect the catheter. To contract two inches under heat, the control member would need to be several times that 2 inch contraction distance. In the case of a strand of Flexinol wire which shrinks about 6% when heated, the strand may require heating a wire that is about 12 inches or more in length, which will be difficult to fit in the distal portion. In addition to installing the heat sensitive control member, a heat source will need to be placed in the catheter which could undesirably increase the size of the catheter; even in the instance where the heat source is pair of electrical wires, the current demands may be sufficiently high to require wire having sufficient size to carry the amperage, which in some cases may be 1 amp or higher. In the event that a cooling source is also desired, the catheter size would be further increased. In many applications, decreasing the size of the catheter is necessary and desirable for the specific application, especially whenever the catheter is being used intravascularly.

Moreover, the heat that is necessary to contract the control member can alter the controlled ablation process by introducing significant additional heat into the distal portion of the catheter. Keep in mind that an effective ablation lesion typically occurs when the tissue reaches approximately 50° C. Generally speaking, it is desirable to supply only enough heat as is necessary to achieve an effective ablation lesion (i.e., to raise the tissue temperature to around 50° C.); applying energy in excess of that threshold may cause undesirable problems such as charring, tissue pop, etc. which can occur when tissue temperature exceeds about 55° C.

To induce the control member to contract may require application of sufficient heat to increase the temperature of the control member in excess of about 78° C. and in some instances in excess of about 98° C. This kind of heat can alter and/or influence the timing requirements for a process to create an effective ablation lesion. In the circumstances where the control member comprises a wire, to locate the wire in the catheter could deliver a substantial amount of energy into the vasculature.

In addition, where the heat source is a pair of electrical conductors, the current demands can be larger than those that are typically used in most intra-body catheters. Accordingly, additional measures of electrical isolation may be needed, which could also adversely increase the size of the catheter and/or reduce the flexibility of the catheter.

For all the reasons discussed above, it is problematic to try and utilize a catheter that has a heat-contractive member in the distal portion of a catheter to control the deflection of the catheter.

The present invention overcomes these disadvantages by removing the heat sensitive control member and its active heat source from the distal portion of the catheter, instead placing them in the control unit (or even the handle) of the catheter. Heating the heat-sensitive control member outside the body (e.g., in the control unit or the handle) does not complicate the controlled ablation process and it permits more precise control over the catheter. Unlike a catheter, the control unit often has no size constraints. Once the heat-sensitive control member is located inside the control unit, a variety of simple and complex configurations may be used, including for example, pulleys, springs, and other such mechanisms, to accommodate the properties and characteristics of the heat sensitive element.

One of ordinary skill will appreciate that the length of the control member will depend upon the material being used for the control member, the displacement of the elongate tensioning element that is desired, and the configuration of the control unit. For example, if a catheter includes a pull wire that must be linearly displaced by about three-quarters of an inch in order to fully deflect the catheter, then a variety of configurations may be used. If Flexinol™ wire of a particular diameter is used as the control element, where it is known that Flexinol™ wire of that diameter contracts by about 5% during heating, then to achieve three-quarters of an inch displacement will require a length of Flexinol™ wire as follows:

Length $L=(0.75$ inches$)/0.05=15$ inches

This length may dictate that the control unit be at least 15 inches long, or if the embodiment described in FIG. 2 is used, the length of the control unit may be cut by as much as about 50% by using a single pulley, or more if additional pulleys are used.

If the control member is to be made of a helix having a negative coefficient of thermal expansion, for example a BMX series biometal helix, then the control member may be much shorter. Because the helix configuration achieves a much higher contraction rate (as much as about 30% to about 70% of the overall length), a control member as short as about 1.1 inches to about 2.5 inches may be used, depending upon the diameter of the wire, the diameter of the helix and the characteristics of the wire being used.

Although at least four embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A deflectable catheter comprising:
a catheter body having a proximal end, a catheter shaft, and a distal portion,
a control unit coupled to the proximal end of the catheter body;
an elongate tensioning element that extends from the control unit through the proximal end, the catheter shaft and to the distal portion of the catheter body, said elongate tensioning element being secured at a point in the distal portion such that when pulled, the distal portion deflects;
a heat-sensitive control member located in the control unit and coupled to a proximal end of the elongate tensioning element; and
a heat source positioned to apply heat to the heat-sensitive control member;
wherein the heat-sensitive control member has a negative coefficient of thermal expansion such that when heat is applied to the heat-sensitive control member, the heat-sensitive control member contracts, places the elongate tensioning element in tension, and deflects the distal portion of the catheter.

2. The deflectable catheter of claim 1 wherein the heat source comprises:
a first conductor electrically coupled to a proximal end of the heat-sensitive control member;
a second conductor electrically coupled to a distal end of the heat-sensitive control member; and
a power supply electrically coupled to the first and second conductors to deliver an amount of current to the heat-sensitive control member such that the heat-sensitive control member is heated to a state where the heat-sensitive control member contracts.

3. The deflectable catheter of claim 2 wherein the heat-sensitive control member comprises a nickel titanium alloy.

4. The deflectable catheter of claim 3 wherein the control unit comprises at least one pulley, and wherein the heat-sensitive control member is wrapped about a portion of the at least one pulley and is sufficiently long such that when heat is applied, the wire will contract to a distance that deflects the distal portion of the catheter by at least about 180 degrees.

5. The deflectable catheter of claim 2 wherein the heat-sensitive control member comprises a nickel titanium alloy formed in a helix shape.

6. The deflectable catheter of claim 5 wherein one end of the helix is secured to the control unit, and the other end of the helix is coupled to the elongate tensioning element using a non-thermally and non-electrically conductive material.

7. The deflectable catheter of claim 5 wherein the control unit comprises a catheter handle adapted to fit within a hand of an operator.

8. The deflectable catheter of claim 2 further comprising a temperature sensor to measure the temperature of the heat-sensitive control member.

9. The deflectable catheter of claim 8 further comprising a processor to estimate an amount by which the catheter has been deflected based in part on an output of the temperature sensor.

10. The deflectable catheter of claim 1 further comprising a coupler to couple a distal end of the heat-sensitive control member to the proximal end of the elongate tensioning element, said coupler providing thermal and electrical isolation between the heat-sensitive control member and the elongate tensioning element.

11. The deflectable catheter of claim 1 further comprising:
a cooling source positioned to remove heat from the heat-sensitive member;
such that as heat is removed from the heat-sensitive control member, the heat-sensitive control member expands and deflects the distal portion of the catheter.

12. A method of deflecting a catheter comprising:
providing a catheter having
a catheter body with a proximal end, a catheter shaft, and a distal portion,
a catheter control handle coupled to the proximal end of the catheter body;
an elongate tensioning element that extends from the control handle through the proximal end, the catheter shaft and to the distal portion of the catheter body, said elongate tensioning element being secured at a point in the distal portion such that when pulled, the distal portion deflects; and
an elongate flexible member having a negative coefficient of thermal expansion disposed in the control handle and coupled to a proximal end of the elongate tensioning element; and
heating the elongate flexible member in the catheter control handle to cause the elongate flexible member to contract and pull the elongate tensioning element to deflect the catheter.

13. The method of claim 12 wherein heating the elongate flexible member comprises: applying a current to the elongate flexible member by coupling a power supply to a first terminal coupled to a first end of the elongate flexible member and to a second terminal coupled to a second end of the elongate flexible member.

14. The method of claim 12 wherein heating the elongate flexible member comprises:
heating the elongate flexible member to a point where it contracts a distance that deflects the catheter at least 180 degrees.

15. The method of claim 12 wherein the elongate flexible member comprises a nickel titanium alloy.

16. The method of claim 12 wherein the catheter handle has at least one control knob, wherein the step of heating the elongate flexible member in the catheter control handle comprises:
adjusting the control knob to apply heat to the elongate flexible member in the catheter control handle to deflect the catheter.

17. The method of claim 12 further comprising:
heating the elongate flexible member to a plurality of increasing temperatures;
measuring an amount of deflection of the distal portion of the catheter at each of the plurality of increasing temperatures, and associating each measured amount of deflection with the temperature at which the deflection was measured; and
storing the associated temperature and deflection measurements in a storage medium.

18. The method of claim 17 further comprising:
heating the elongate flexible member in the catheter control handle;
measuring a temperature of the heated elongate flexible member; and
using the measured temperature and the stored associated temperature and deflection measurements to estimate an amount by which the catheter has been deflected.

19. The method of claim 17 further comprising:
allowing the elongate flexible member to cool to a plurality of decreasing temperatures;
measuring an amount of deflection of the distal portion of the catheter at each of the plurality of decreasing temperatures, and associating each measured amount of deflection with the temperature at which the deflection was measured and associating a status flag to indicate that the deflection was measured at a decreasing temperature; and
storing the associated temperature and deflection measurements in a storage medium;
wherein the step of measuring an amount of deflection of the distal portion of the catheter at each of the plurality of increasing temperatures comprises:
measuring an amount of deflection of the distal portion of the catheter at each of the plurality of increasing temperatures, and associating each measured amount of deflection with the temperature at which the deflection was measured and associating a status flag to indicate that the deflection was measured at an increasing temperature.

20. The method of claim 12, further comprising:
heating the elongate flexible member in the catheter control handle;
measuring a resistance of the elongate flexible member using two electrodes on opposite ends of the heated elongate flexible member;
using the measured resistance to estimate an amount by which the catheter has been deflected.

21. The method of claim 12 further comprising:
heating the elongate flexible member to deflect the catheter to each of a plurality of deflected positions;
measuring a resistance of the elongate flexible member using two electrodes on opposite ends of the heated elongate flexible member, for each of the plurality of deflected positions;
measuring an amount of deflection of the catheter at each of the plurality of deflected positions, and associating each measured amount of resistance with the measured amount of deflection for each of the plurality of deflected positions;
storing the associated resistance and deflection measurements in a storage medium;
heating the elongate flexible member in the catheter control handle;
measuring a resistance of the elongate flexible member using two electrodes on opposite ends of the heated elongate flexible member;
using the measured resistance and the stored associated resistance and deflection measurements to estimate an amount by which the catheter has been deflected.

22. The method of claim 12 further comprising:
removing heat from the elongate flexible member in the catheter control handle to cause the elongate flexible member to expand, resulting in a deflection of the catheter.

23. A method of manufacturing a deflectable catheter comprising:
forming a catheter having a catheter body with a proximal end, a catheter shaft, a distal portion, and an elongate tensioning element that extends from the proximal end through the catheter shaft and to the distal portion of the catheter body, said elongate tensioning element being secured to the catheter such that a force imposed on the elongate tensioning element causes the catheter to defect;
forming a catheter control unit;
positioning a control member inside the control unit such that one end of the control member is fixed relative to the control unit and the other end is free to move with respect to the control unit, said control member having a negative coefficient of thermal expansion such that when heat is applied, the control member contracts; and
providing a heat source within the control unit such that when activated, the heat source heats the control member and causes it to contract;
securing the catheter to the control unit; and
positioning the elongate tensioning element into mechanical communication with the control member such that when the control member is heated, a force is imposed on the elongate tensioning element to cause the catheter to deflect.

24. The method of manufacturing a deflectable catheter of claim 23 wherein the step of providing a heat source comprises:
installing a first conductor into the control unit that is electrically coupled to a proximal end of the control member;
installing a second conductor into the control unit that is electrically coupled to a distal end of the control member; and
providing a connector electrically coupled to the first and second conductors which can be connected to a power supply for delivering sufficient current to the control member to heat the control member.

25. The method of manufacturing a deflectable catheter of claim 23 wherein the control member comprises a nickel titanium alloy.

* * * * *